US009033971B2

(12) United States Patent
Hancock

(10) Patent No.: US 9,033,971 B2
(45) Date of Patent: May 19, 2015

(54) SURGICAL ANTENNA AND ELECTROSURGICAL SYSTEM USING THE SAME

(75) Inventor: Christopher Paul Hancock, Bristol (GB)

(73) Assignee: CREO MEDICAL LIMITED, Somerset (GB)

( * ) Notice: Subject to any disclaimer, the term of this patent is extended or adjusted under 35 U.S.C. 154(b) by 592 days.

(21) Appl. No.: 13/378,552

(22) PCT Filed: Jul. 20, 2010

(86) PCT No.: PCT/GB2010/001376
§ 371 (c)(1),
(2), (4) Date: Mar. 19, 2012

(87) PCT Pub. No.: WO2011/010089
PCT Pub. Date: Jan. 27, 2011

(65) Prior Publication Data
US 2012/0172865 A1 Jul. 5, 2012

(30) Foreign Application Priority Data
Jul. 20, 2009 (GB) .................................. 0912577.4

(51) Int. Cl.
*A61B 18/18* (2006.01)
*H01Q 21/08* (2006.01)
(Continued)

(52) U.S. Cl.
CPC ................ *H01Q 21/08* (2013.01); *A61B 18/18* (2013.01); *A61B 18/1815* (2013.01); *A61B 2018/1853* (2013.01); *H01Q 1/22* (2013.01); *H01Q 1/42* (2013.01); *H01Q 3/24* (2013.01); *H01Q 21/0075* (2013.01)

(58) Field of Classification Search
USPC ...................................................... 606/22–45
See application file for complete search history.

(56) References Cited

U.S. PATENT DOCUMENTS 5,057,106 A * 10/1991 Kasevich et al. ............... 606/33
6,287,302 B1 9/2001 Berube
(Continued)

FOREIGN PATENT DOCUMENTS

EP 1 810 625 A1 7/2007
EP 2 106 763 A1 10/2009
(Continued)

OTHER PUBLICATIONS

Office Action, International Patent Application No. 201080032496.0 issued Nov. 6, 2013.
(Continued)

*Primary Examiner* — Rex R Holmes
(74) *Attorney, Agent, or Firm* — Arent Fox LLP

(57) ABSTRACT

A surgical spatula (10, 34) has a flat paddle (38, 62) and a handle extending away from a first end of the flat paddle (38, 62). The handle has a coaxial power feed (64, 130) which is connectable to receive energy from a microwave power source. The paddle (38, 62) contains a microwave conveying structure connected to the coaxial power feed (64, 130). The microwave conveying structure is enclosed at a front end of the paddle (38, 62) opposite to the first end so that microwave radiation is blocked from being emitted from the front end. The microwave conveying structure is open along a side of the paddle (38, 62) which extends away from the first end to permit a microwave radiation field to be emitted from that side.

9 Claims, 4 Drawing Sheets

(51) Int. Cl.
*H01Q 1/22* (2006.01)
*H01Q 1/42* (2006.01)
*H01Q 3/24* (2006.01)
*H01Q 21/00* (2006.01)

(56) References Cited

U.S. PATENT DOCUMENTS

| | | |
|---|---|---|
| 2001/0025190 A1 | 9/2001 | Weber et al. |
| 2003/0144653 A1 | 7/2003 | Francischelli et al. |
| 2003/0212395 A1* | 11/2003 | Woloszko et al. ............ 606/41 |
| 2004/0049254 A1 | 3/2004 | Longo |
| 2005/0203499 A1 | 9/2005 | Pendekanti et al. |
| 2005/0273097 A1 | 12/2005 | Ryan |
| 2006/0081565 A1 | 4/2006 | Lee et al. |
| 2008/0221650 A1 | 9/2008 | Turner et al. |
| 2008/0319434 A1 | 12/2008 | Rick et al. |
| 2009/0143808 A1* | 6/2009 | Houser ..................... 606/170 |
| 2010/0004650 A1 | 1/2010 | Ormsby et al. |
| 2010/0286686 A1 | 11/2010 | Hancock |
| 2010/0331838 A1 | 12/2010 | Ibrahim et al. |

FOREIGN PATENT DOCUMENTS

| | | |
|---|---|---|
| EP | 2 174 613 A1 | 4/2010 |
| EP | 2 255 742 A1 | 12/2010 |
| GB | 2472012 A | 1/2011 |
| GB | 2472972 A | 3/2011 |
| JP | 2003-523799 A | 8/2003 |
| JP | 2009-517130 A | 4/2009 |
| WO | WO 02/061880 A2 | 8/2002 |
| WO | WO 03/063717 A1 | 8/2003 |
| WO | 1489807 A | 4/2004 |
| WO | WO 2004/047659 A2 | 6/2004 |
| WO | WO 2006/111192 A1 | 10/2006 |
| WO | WO 2006/127847 A2 | 11/2006 |
| WO | WO 2007/061984 A2 | 5/2007 |
| WO | WO 2008/043997 A1 | 4/2008 |
| WO | WO 2008/044000 A1 | 4/2008 |
| WO | 2009-517130 A | 4/2009 |
| WO | WO 2009/040523 A2 | 4/2009 |
| WO | WO 2009/062057 A2 | 5/2009 |
| WO | WO 2011/010086 A1 | 1/2011 |

OTHER PUBLICATIONS

Search Report, International Patent Application No. 201080032496.0 dated Oct. 29, 2013.

Robert Paglione et al., "Microwave Applicators for Localized Hyperthermia Treatment of Malignant Tumors." IEEE MIT-S International Microwave Symposium Digest, May 28-30, 1980, pp. 351-354.

Buck Walter, Conference Proceedings-European Microwave Conference 1978, Microwave Exhibit and Publ Ltd, Sep. 4-8, 1978, pp. 548-552.

Search Report, International Patent Application No. PCT/GB2010/001376 dated Jan. 27, 2011.

* cited by examiner

SURGICAL ANTENNA AND ELECTROSURGICAL SYSTEM USING THE SAME

CROSS-REFERENCE TO RELATED APPLICATIONS

This application is a National Stage entry of International Application No. PCT/GB2010/01376, filed Jul. 20, 2010, which claims priority to British Patent Application No. 0912577.4 filed Jun. 9, 2009. Each of the proceeding applications is incorporated in its entirety by reference herein.

FIELD OF THE INVENTION

The invention relates to apparatus for using microwave radiation in the treatment of biological tissue. For example, the invention may be applied as a surgical antenna for delivering microwave energy to biological tissue structures contained within the human or animal body.

BACKGROUND OF THE INVENTION

At certain frequencies, microwave energy can produce controlled ablation of biological tissue. For example, microwave energy having a frequency between 14 and 15 GHz has a relatively limited depth of penetration into biological tissue, which is beneficial for ablation control.

WO 2004/047659 and WO 2005/115235 disclose apparatus for and methods of both controllably ablating biological tissue and measuring information about tissue type and/or state using microwave radiation. These documents disclose the benefits of performing dynamic impedance matching between the energy source and the tissue.

WO 2008/044000 discloses a radiating scalpel suitable for use with the ablation apparatus mentioned above. The scalpel comprising an antenna arranged to emit a substantially uniform microwave radiation field along the cutting edge (i.e. blade) of the scalpel. The emitted microwave radiation is able to cauterise biological tissue during cutting, which facilitates invasive surgery performed on highly vascularised organs such as the liver.

SUMMARY OF THE INVENTION

At its most general, the present invention provides one or more radiating side edges and/or one or more radiating faces (top and/or bottom) on a surgical spatula, in particular a spatula sized to be insertable invasively by an endoscope or a proctoscope or any other scoping device that contains a channel or flexible tube to enable an electrosurgical instrument to be introduced (e.g. in laparoscopic procedures or through natural orifices).

A spatula is a different type of surgical tool from the scalpel disclosed in WO 2008/044000. A spatula is typically characterised by a flat paddle that extends away from a handle. In the invention, the front edge of the paddle (i.e. the edge at a side opposite the handle) is rounded (i.e. blunt) to facilitate safe insertion of the spatula into the body, e.g. through a suitable orifice or along the instrument channel of an endoscope. The radiating side edge may be used to ablate tissue and/or assist with cutting and simultaneous sealing of tissue when the spatula has reached its destination.

According to a first aspect, the invention may provide a surgical spatula comprising a flat paddle and a handle extending away from a first end thereof, wherein the handle comprises a coaxial power feed connectable to receive energy from a microwave power source, and the paddle contains a microwave conveying structure connected to the coaxial power feed, the microwave conveying structure being enclosed at a front end of the paddle opposite the first end and open along a side of the paddle which extends away from the first end to permit a microwave radiation field to be emitted from that side. The invention may thus provide a spatula arranged to radiate microwave energy along one or both sides that extend substantially in the same direction as the handle. These sides of the spatula include for example the narrow side edges and the flat surfaces (hereinafter "faces") of the paddle. Any one or more of these sides or faces may radiate microwave energy in the invention. The frequency of the microwave energy and the configuration of the microwave conveying structure may be arranged based on known properties of tissue to be treated (i.e. ablated) to cause the spatula to radiate microwave energy in a substantially uniform focussed and controlled manner. The focussed behaviour may result from selecting the frequency and configuring the structure such that microwave energy radiates into the tissue with a depth of penetration of between 1 mm and 5 mm, but do not radiate substantially into free space (air). Possible uses for a spatula having these features are discussed below.

The microwave conveying structure may be a stripline (i.e. triplate) structure. The stripline structure may include a microwave circuit having a plurality of radiating elements located at the (or each) open side edge of the paddle. Each radiating element may comprise a patch of conducting material adjacent the open side edge. Each radiating element may have a predetermined impedance selected to inhibit radiation into free space but promote radiation into biological tissue. The predetermined impedance may be substantially the same as the impedance of biological tissue to be treated or may be the complex conjugate thereof. The microwave circuit may include an impedance transformer arranged to match the impedance of the coaxial power feed to the predetermined impedance. This structure may minimise radiation emissions into free space. This feature may be particularly important in a spatula where both side edges are open. Only one edge may be in contact with tissue at any point in time; radiation is inhibited at the open edge exposed to free space (which prevents unintentional effects) but occurs at the edge where there is contact with tissue.

The microwave radiation field may have a frequency between 500 MHz and 100 GHz. For example, the spatula may emit microwave radiation in any one or more of the following frequency bands: 900 MHz to 1.5 GHz, 2.2 GHz to 2.45 GHz, 5.725 GHz to 5.875 GHz, 14 GHz to 15 GHz, and 24 GHz to 24.25 GHz. Spot frequencies of 2.45 GHz, 5.8 GHz, 14.5 GHz, or 24 GHz may be used. A first advantage associated with using spot frequency sources rather than sources that operate over a band of frequencies is the ability to fabricate impedance or matching transformer structures with exactness, i.e. the physical geometry for transformers that are a quarter (or odd multiples thereof) or a half (or multiples thereof) wavelengths can be realised exactly at one frequency only. A second advantage is that higher 'Q' structures (or resonators) may be realised when the quarter wavelength or the half wavelength can be defined and fabricated with exactness.

It may be advantageous to use higher frequency microwave radiation, e.g. 24 GHz, 31 GHz or more, to implement the radiating spatula due to the shorter wavelengths associated with the higher microwave frequencies help ensure that the microwave field and related tissue effects are uniform. This is of particular interest where the size of the blade must be minimised in order for it to fit inside small orifices within the human body or dedicated instrument channels contained within various laparoscopes. High microwave frequency energy also implies small depth of penetration of the energy by radiation, which enables the tissue effects to be controllable or allows the energy to be focussed into the tissue of interest.

The open side edge of the spatula may be sharp to be suitable for cutting. In contrast, the front end (opposite the handle) may be smooth to be unsuitable for cutting. This feature may prevent accidental cutting during insertion of the spatula.

The spatula may be used invasively. In another aspect, the invention may provide a surgical instrument comprising an endoscope and a surgical spatula as describe above, wherein an instrument channel of the endoscope carries a coaxial power cable, and the handle of the spatula is mountable at the distal end of the instrument channel to connect the coaxial power feed to the coaxial power cable. The spatula may thus protrude from the end of the endoscope and hence be capable of being manipulated through control of the endoscope, e.g. via steering mechanisms located at the proximal end of the instrument.

The width of the spatula may be less than 4 mm to allow it to be used in regions of the body where access is restricted. Indeed the overall dimensions of the spatula may need to be selected to be suitable for invasive use. For example, the spatula may be sized to enable it to travel through the instrument channel of an endoscope. The inner diameter of an endoscope's instrument channel is typically 3 mm. The spatula may therefore have a maximum width of less than 3 mm, e.g. 2.8 mm, to permit it to be introduced into the endoscope by inserting its distal end through the proximal end of the endoscope's instrument channel. In other embodiments, the spatula may be inserted into the distal end of the instrument channel before the endoscope is inserted into the body. In such embodiments the width of the paddle may be greater than the diameter of the instrument channel, e.g. having a maximum greater than 3 mm, such as 6 mm or 8 mm.

The length and thickness of the spatula may be selected in relation to the width to provide a paddle-like configuration. For example, where the maximum width is 2.8 mm, the length may be 10 mm or less and the thickness may be 1.5 mm or less.

The handle may be adapted to fit tightly into the distal end of the instrument channel so that it can be steered or manipulated using the mechanical controls located at the proximal end of the endoscope. The handle may include a separable adaptor, e.g. a sleeve, made of insulating material (e.g. plastic) for performing a dual function of securing the radiating structure to a flexible or semi-flexible microwave feed cable carrying energy from the microwave energy source through the instrument channel and preventing leakage of energy (e.g. due to the junction radiating) from the endoscope at the interface between the microwave power feed cable and the coaxial power feed on the spatula. For example, the handle may be tapered to form an interference fit in the distal entry port of the instrument channel. Alternatively, the adaptor may have a keyway formed therein for securing a corresponding key formed on the handle to lock the spatula relative to the endoscope for ease of use or manipulation within the body. The key and lock mechanism may offer the ability to insert the instrument down the instrument channel with ease and then locking or securing the radiating section into position once it reached the distal end.

The flexible or semi-flexible microwave feed cable may be up to 2.5 m in length. In one embodiment, the cable may comprise two sections: a first section having a first diameter for delivering microwave energy from a microwave generator to a region close to the endoscope, and a second section having a second diameter smaller than the first diameter for fitting into the instrument channel of the endoscope.

The stripline structure may comprise a sandwich of conductive layers (e.g. layer of metallization) and insulating layers (e.g. layers of dielectric material) arranged to allow microwave fields to emanate from selected edges e.g. to cause controlled tissue destruction. The microwave radiation field may be in the form of fringe fields from a plurality of radiators (e.g. the plurality of radiating elements) positioned at the open edge of the paddle.

The handle may comprise a rigid coaxial cable separate from and attachable to the paddle. Alternatively, the handle and paddle may both be formed by a single stripline structure.

The stripline structure may physically resemble a spatula paddle. A stripline launcher, e.g. an SMA stripline launcher, may be included at one end to enable a coaxial cable to be connected to the paddle. The stripline launcher may have a female or male SMA microwave connector at one end and a flat tab at the other end arranged to fit inside the stripline sandwich structure to contact with the central conductive layer (microwave circuit), which may be a microstrip line, a strip-line or the like. The tab/strip-line interface preferably forms a good impedance match (or has a voltage standing wave ratio close to 1:1) to allow for the majority of the energy conveyed by the coaxial cable, e.g. from a microwave generator to be launched into the stripline structure. This invention is not limited to using a SMA launcher, i.e. other commonly available microwave connectors may also be used, e.g. MCX, 3.5 mm, 2.4 mm, SMB, BMA, SMC, SMS, MMBX, MMCX, MMPX 1.0/2.3QNA, etc.

In detail, the stripline structure may comprise a flat profile having the following layers in sequence: a first conductive layer, a first insulating layer (e.g. formed from a dielectric material), the microwave circuit (e.g. a pattern of metallisation on the first insulating layer), a second insulating layer (of the same or different dielectric material as the first insulating layer), and a second conductive layer.

The microwave circuit may be etched from a layer of metallization formed on one side of the first or second dielectric material or formed on both materials, such that when they are sandwiched together the thickness of metallization will be doubled.

The first and/or second conductive layers may be layers of metallisation formed on the outer surface of the first and second insulating layers. The first and second conductive layers are electrically connected along the sides of the paddle in a manner to prevent emission of microwave radiation therefrom.

As an alternative to the stripline structure, the microwave conveying structure may comprise a monolithic piece of metallised ceramic in the shape of a spatula paddle. The paddle may be arranged to receive power from a coaxial feed, e.g. by having a metallised outer surface for connecting to an outer conductor of a coaxial feed and a passageway for receiving an inner conductor of a coaxial feed, e.g. as an E-field monopole or an H-field loop. In this arrangement, the microwave energy may be fed into the ceramic to cause electromagnetic fields to radiate regions of the outer surface that are not metallised. For example, the structure may be arranged to radiate along either one or both of the edges that are perpendicular to the end where the coaxial feed is connected. The ceramic may be metallised using silver, copper, gold or brass.

In this arrangement, the ceramic paddle may be made cylindrical at the feed end to enable it to be fitted inside a rigid coaxial cable structure. The ceramic coaxial structure may be modelled using suitable electromagnetic field simulation tools to enable the radiating ceramic to be impedance matched with the impedance of the coaxial feed line when the radiation edge is in contact with the biological tissue (the load). Similarly, the radiating ceramic may be arranged to mismatch with air or other types of tissue. The ceramic section located inside the coaxial structure may form an impedance matching transformer, for example a quarter wave (or odd multiple thereof) transformer to enable a coaxial structure that uses a low permittivity material to be matched with the high permittivity of the biological tissue.

The ceramic paddle may be formed from sapphire. Other materials may include alumina (sapphire impregnated with glass) or other ceramic materials, such as zirconia, that exhibit a low dissipation factor (or loss) and a high dielectric constant at the frequency of interest.

For efficient coupling to be achieved, the length of the ceramic paddle may be 10 mm or less.

The microwave conveying structure may provide a controllable energy supply for each open side or face of the paddle. For example, where the spatula has more than one open side or face, each open side or face may have a respective stripline structure, connected to receive microwave energy via a power splitting network, e.g. in the handle or paddle. The microwave generator may be arranged to detect reflected signals from the spatula to detect either a mismatched condition (open side in air) or a matched condition (open side in tissue). The microwave generator may be arranged to control the power level of each independently controllable microwave energy supply based on the detected condition. For example, the microwave generator may switch off the microwave energy supply that feeds energy into a mismatched edge or face. Alternatively, the microwave generator may divert the energy on an energy supply to a mismatched edge or face to an edge or face that is matched. This effect may also be achieved by providing a balanced feed structure for a plurality of radiating elements on a stripline structure.

The spatula may be used to carry out key-hole surgery using the natural orifice translumenal endosurgery (NOTES) technology, based on the concept of incisionless surgery and a transgastric or even transcolonic approach for intra-abdominal surgery.

BRIEF DESCRIPTION OF THE DRAWINGS

Examples of the invention are described in detail below with reference to the accompanying drawings, in which.

DETAILED DESCRIPTION; FURTHER OPTIONS AND PREFERENCES

Figure 1:
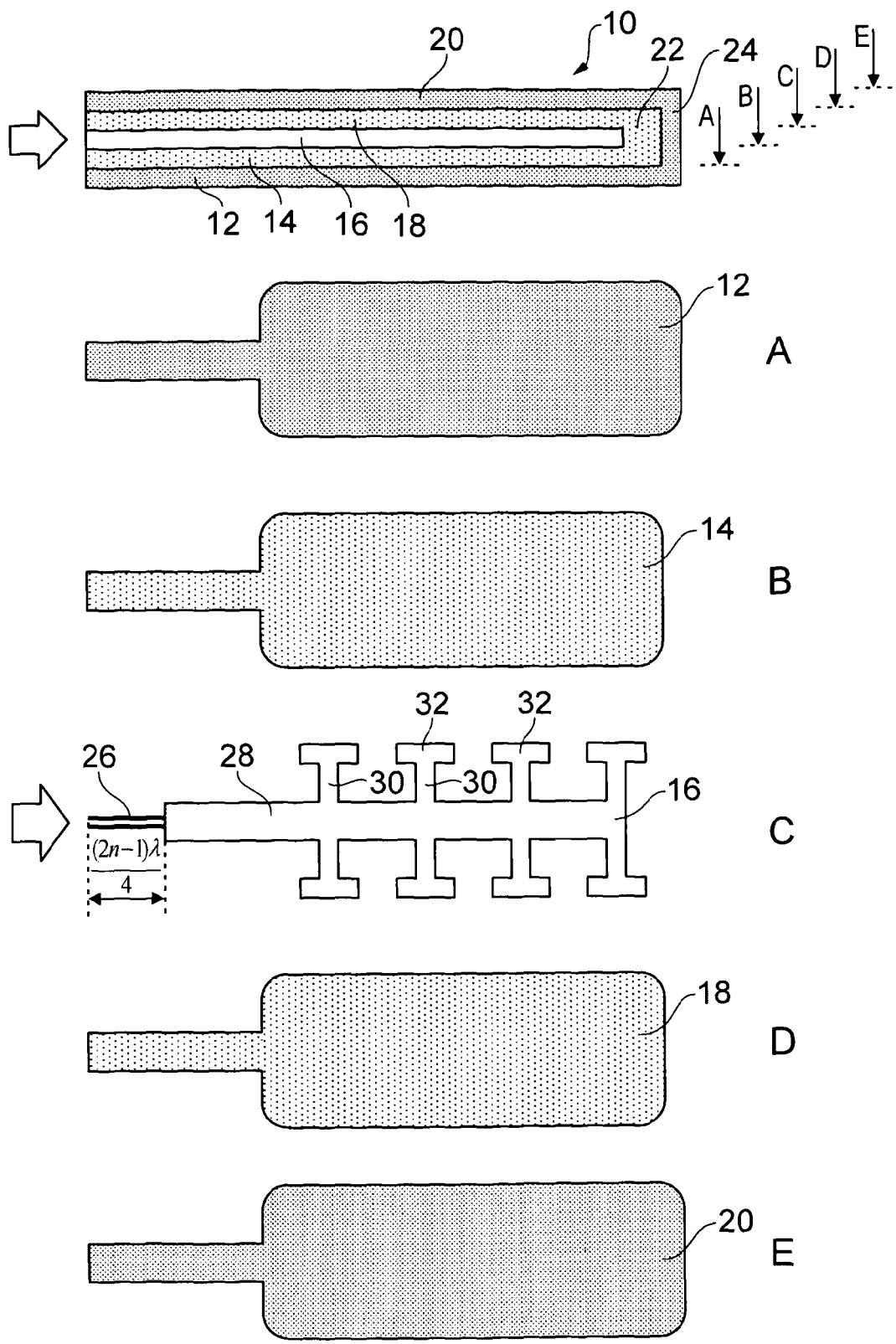
FIG. 1 shows various cross-sectional views of a radiating spatula that is an embodiment of the invention.

FIG. 1 shows a surgical spatula 10 comprising a paddle containing a stripline structure arranged to emit a microwave radiation field along both side edges of the paddle. The top panel in FIG. 1 is a schematic cross-sectional view of the spatula which shows the sandwiched layers of the stripline structure. The remaining panels A-E in FIG. 1 are plan views of each layer looking at the direction indicated by arrows A-E in the top panel.

The spatula 10 in FIG. 1 is composed entirely of a layered stripline structure. The stripline structure includes a first conductive layer 12, first insulating layer 14, microwave circuit layer 16, second insulating layer 18 and second conductive layer 20 stacked on top of one another in that order. The conductive and insulating layers 12, 14, 18, 20 are each shaped roughly as a flat oblong paddle with an elongate handle extending from the centre of one of the short sides. The microwave circuit layer 16 is patterned to perform the radiating and energy coupling functions described in detail below.

At the short side of the oblong paddle opposite to the handle, the stripline structure is closed to prevent radiation from being emitted therefrom. In this embodiment the closure is achieved by providing an insulating link portion 22 connecting the first and second insulating layers 14, 18 and a conductive link portion 24 (e.g. metal filler) which covers and electrically connects the first and second conductive layers 12, 20.

The shape of the paddle is not restricted to that shown in FIG. 1. For example, the paddle may be flat with rounded ends, flat with a tapered blade, or have a trough profile. Other shapes that may be of interest include Trulla and Chattaway (or any other standard spatula shape).

When considering the most appropriate stripline structure to use in practice, a compromise must be made between the following factors:

(1) a track width able to accommodate a microwave circuit having sub-components such as an impedance matching transformer, feed lines and radiating lines in such a way to ensure that the radiating edges of the spatula can deliver the required level of microwave power to cause controlled tissue ablation, e.g. to ablate the stems of polyps to facilitate their removal or prevent further growth;

(2) dielectric material thickness within a range to preserve suitable spatula dimensions, i.e. to ensure that the device is clinically useful; and (3) dielectric material loss tangent (tan δ) or dissipation factor low enough (at the frequency of operation) to ensure that a large portion of the microwave energy is not lost or dissipated within the dielectric material, i.e. lost as heat and absorbed by the material. This loss may lead to structural heating, which may cause damage to healthy tissue structures, and is therefore most undesirable.

The dielectric material preferably has a low dielectric constant since the line width reduces as the dielectric constant increases. A suitable material may be an RT/duriod material (e.g. RT/duroid 5880) from Rogers Corporation. The dielectric material may have a dielectric constant of 2.2 or less and a loss factor (tan δ) of 0.0009 or less e.g. at a operation frequency of 10 GHz. RT/duroid 5880 material comes in a range of standard dielectric thicknesses e.g. from 0.127 mm to 3.175 mm. The thickness used for the first and second insulating layers in the present embodiment may be between 0.05 mm and 0.5 mm, preferably between 0.175 mm and 0.254 mm.

For the design of the microwave circuit 16, it is preferable to use low impedance lines, for example, lines with a characteristic impedance of less than 50Ω, in order to ensure that low thickness dielectric materials may be used and that the widths are such that it is possible to carry levels of microwave power necessary for the desired tissue effects to be produced when the microwave energy emanates out of the spatula along the edges. As characteristic impedance of a line made from a given material reduces, the width of the line increases. Stripline structures are shielded structures in which spurious or leakage radiation is negligible. In the invention this feature may prevent radiation leaking out from regions of the structure where it is undesirable for EM fields to be generated, whilst permitting radiation at certain locations along the edges where it is required for the fields to be generated. Synthesis equations for configuring stripline structures, which enable the width of the lines to be calculated for specified dielectric thickness, variations of the thickness of the metallic microwave circuit and variations in the dielectric constant of the dielectric materials are known and commonly used by practicing microwave engineers.

Three examples of how the above principles may be applied are:

(1) a 10Ω stripline structure provided by a line width of 2.95 mm sandwiched between layers of RT/duroid 5880 material with a dielectric constant of 2.2 and a dielectric thickness of 0.254 mm;

(2) a 5Ω stripline structure provided by a line width of 6.18 mm sandwiched between layers of RT/duroid 5880 material with a dielectric constant of 2.2 and a dielectric thickness of 0.254 mm; and (3) a 5Ω strip-line structure provided by a line width of 3.07 mm sandwiched between layers of RT/duroid 5880 material with a dielectric constant of 2.2 and a dielectric thickness of 0.127 mm.

Conventional surgical spatulas are made from medical grade stainless steel. In the present invention the first and second conductive layers 12, 20 may be each be part of a stainless steel body. For example, two identical stainless steel spatulas may be milled down until slightly less than half the structure remains (slightly less to allow for the two layers of dielectric material and the microwave circuit to be included), or special purpose half spatulas will be made that can accept the two layers of dielectric material and the microwave circuit. Due to the fact that stainless steel is not a good electrical conductor, the first and second conductive layers may be layers of metallisation plated on the inner faces of the stainless steel body. The layer of metallisation may be copper, gold, silver, aluminium or brass. If it is impractical to plate the stainless steel, then it may be possible or more desirable to bond a layer of metallization onto the outside surface of the two dielectric materials (using a thin (less than 10 μm) layer of low loss adhesive). Alternatively, the low loss material may be plated onto the stainless steel body. The thickness of the stainless steel portions carrying the first or second conductive layer may be between 0.25 mm and 1 mm. Alternatively, aluminium may be used for the conductive layers and the outer housing of the spatula paddle. In this case, additional metallisation layers may not be required.

The microwave circuit 16 may be a self-supporting separate layer, or may be fabricated, e.g. etched into a layer of metallisation formed on an inner surface of the first or second or both insulating layers. The insulating layers may be a microwave ceramic material, a PCB substrate or the like.

The layer of metallisation may have a thickness between 1 μm and 100 μm. To carry suitable power levels (e.g. up to 120 W continuous wave at 14.5 GHz), the layer(s) of metallisation mentioned herein may be thick, e.g. 35 μm (1 ozft$^{-2}$) or more, e.g. 70 μm (2 ozft$^{-2}$) or more of electrodeposited copper foil.

A layer of biocompatible material (e.g. Parylene C or PTFE) may be applied to the radiating edge of the spatula. The biocompatible layer may have a thickness of 10 μm or less.

The insulating layers 14, 18 may be made from the same or different dielectric material. For example, RT/duroid 5870/5880 high frequency laminates, RO3000 series or RO4000 high frequency circuit materials made by Rogers Corporation or microwave ceramic material, such as Dynallox, with a dielectric constant of 9.0 and a dissipation factor of 0.00045 at 10 GHz may be used. The RT/duroid 5870/5880 material comprise glass microfiber reinforced PTFE composites that have been developed for stripline and microstrip circuit applications. These materials have a low dissipation factor which makes them useful in applications working in the $K_u$ band and above. These materials may have metal layers (e.g. of thicknesses from 8 μm to 70 μm) formed (e.g. electrodeposited) on each surface. One of the layers may be used as a conductive layer 12, 20 and the other may be etched to provide the microwave circuit 16.

The microwave circuit 16 consists of an impedance matching transformer 26, a network of feed lines 28, 30, and a plurality of radiating structures, which are radiating patches 32 in this embodiment. In other embodiments, the microwave circuit may take the form of a slotted antenna, e.g. a partially metallised piece of ceramic or partially metallised piece of microwave substrate material.

As mentioned above, the microwave circuit 16 may be formed as a separate section or layer that is self supporting, i.e. it may be cut or laser etched from a sheet of appropriate conductive material, e.g. copper or aluminium. Alternatively it may be etched out (or routed out) from a layer of metallisation attached to the first, second or both insulating layers 14, 18. The minimum thickness needed for the metallic material that forms a part of the microwave circuit 16 is determined by the skin depth at the frequency of interest and the microwave power requirements.

The structure of the radiating patches may be modelled using a suitable microwave simulation tool, for example CST Microwave Studio® in order to establish the interaction between the emanating fields and a representative biological tissue model, e.g. to ensure that the radiated field is substantially uniform along the side of the spatula and is efficiently coupled into the biological tissue of interest, i.e. at least 90% of the microwave power radiating or emanating from the spatula antenna is delivered into the tissue.

The layers illustrated in FIG. 1 are attached together to form the spatula. The layers may be glued together using a suitable medical grade adhesive, or may be mechanically connected using, for example, screws, pins, dowels, or small rivets. The spacing between the centres of these fixings means must be such that the microwave fields set up inside the structure are unaffected.

As mentioned above, all non-radiating edges of the spatula are sealed to prevent microwave radiation emissions from regions of the paddle or handle where such emissions are undesirable. An example of such sealing is the conductive link portion 24. The link portion may comprise solder, silver paint, copper tape or other suitable low loss conductive materials. Alternatively, the non-radiating edges can be effectively sealed by placing conductive posts or pins along the edge of the spatula in a manner whereby the spacing between adjacent pins or posts is less than one eighth of the wavelength of the frequency of operation.

Figure 2:
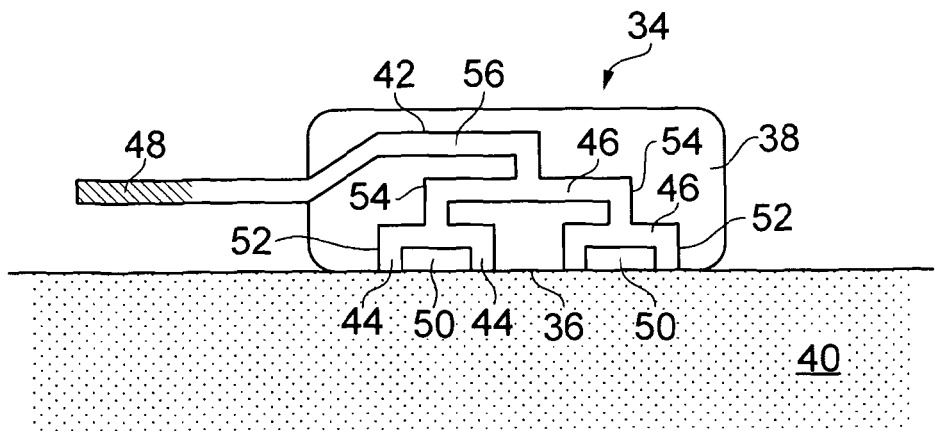
FIG. 2 is a cross-sectional view through a radiating spatula that is another embodiment of the invention and shows the antenna in contact with biological tissue.

FIG. 2 shows a cross-sectional view through a surgical spatula 34 that is another embodiment of the invention. In this embodiment the spatula 34 radiates from only one side edge 36 of the paddle 38. As shown, the radiating edge 36 is in contact with a section of biological tissue 40. The microwave circuit 42 in the spatula is arranged so that the impedance of the radiating section of the spatula is the complex conjugate of the impedance of the tissue. For example, if the impedance of the biological tissue is $R_t+jX_t$ then it is required to make the impedance of the radiating section of the spatula to be equal to $R_t-jX_t$ in order to ensure that the energy emanating from the edge of the radiating spatula is efficiently launched or coupled into the biological tissue, i.e. to minimise any impedance mismatch or reflections that would cause a loss or reduction of energy delivered into the tissue. FIG. 2 illustrates a microwave circuit 42 having four radiating elements 44 arranged at the radiating edge 36. When microwave energy is supplied to the elements 44, a microwave radiation field emanates in the form of fringe fields (see FIG. 5). These fringe fields are used to ablate or selectively destroy the biological tissue 40 at the radiating edge 36.

The feed lines 46 of the microwave circuit 42 in this embodiment may have a characteristic impedance of 5Ω. A quarter-wave impedance transformer 48 is located at the feed end to match a microwave energy generator (not shown) e.g. having an impedance of 50Ω to the 5Ω structure. The value of 5Ω for the transmission feed lines 46 is chosen as an example of a low value that enable the lines to be relatively wide and also provide a direct impedance match with the low impedance of the tissue, hence it should be possible to efficiently launch a large portion of energy from the generator into the tissue 40 without the need to implement additional impedance transformations. The use of wide lines may also be advantageous in terms of ensuring a large electromagnetic field coverage along the length of the paddle, since the field lines will terminate along the edge of the spatula and the fringe fields produced by these lines are used to radiate the tissue to create the desired tissue affect, hence the wider the lines the more field coverage will take place. Moreover, when embodied as a stripline structure feed lines are narrower than in a microstrip equivalent.

The gaps 50 between the radiating elements 44 disposed along the side edge of the paddle should be filled in (e.g. with the dielectric material) to ensure a uniform field distribution along the side edge.

Starting from the radiating edge 36, the radiating patches may be considered as formed by two 5Ω lines 52 each formed in the shape of a U. The radiating elements 44 are at the top of each leg of the U, located at the radiating edge 36. The lengths of the two U lines 52 do not need to be any specific fraction of a wavelength at the frequency of operation, but their lengths should be the same or different by a length that will ensure no phase change between adjacent radiators. A third line 54 with a characteristic impedance of 5Ω is connected to the centre point of the first two lines; the third line may also be formed into a U shape. The third line is configured so that the length of each half (connecting power feed point to each U line 52) is an odd multiple of a quarter of the wavelength of the operation frequency. Each half therefore acts as an impedance transformer. If the tissue load impedance is actually 5±j0Ω, then the impedance seen at the centre of the first two lines will be: 5±j0Ω in parallel with 5±j0Ω, i.e. 2.5±j0Ω. Each arm of the first transformer (the third line 54 with a characteristic impedance of 5Ω)) then transforms the 2.5Ω to ($5^2$/2.5) Ω=10Ω. When the two arms 54 are joined together, the impedance seen at the junction is 10Ω in parallel with 10Ω, i.e. 5Ω. A fourth 5Ω line 56 is connected at the centre (or the junction) of the third line, and this line forms the main feed line between the radiating spatula edge 36 and the proximal end of the structure where a suitable microwave connector (not shown) is located to enable a suitable flexible microwave cable assembly to be used to connect the microwave source (or generator) to the radiating spatula structure. The flexible cable assembly used to feed the spatula with microwave power from the generator will normally have a characteristic impedance of 50Ω, therefore, in order to properly terminate the proximal end of the fourth 5Ω feed line 56 associated with the radiating spatula structure, a third impedance transformer 48 is required to match the 5Ω feed line 56 with the 50Ω external cable (connected between the microwave generator and the radiating spatula structure). This is achieved using a further transmission line structure that has a length equal to an odd multiple of a quarter of the wavelength of the operation frequency and an impedance that is equal to the geometrical mean of the source and load impedances (or equal to the square root of the product of the source and load impedances); in this particular instance, the impedance of the line that performs the transformation is $\sqrt{5 \times 50\Omega}$=15.81Ω.

Implementing the above theory in a stripline structure is straightforward for a skilled person, using known line synthesis techniques.

For example, if a layer of RT/duroid 5880 material to (dielectric constant: 2.2, dissipation factor: 0.0009) having a thickness of 0.254 mm is used with upper and lower metallisation layers each having a thickness of 0.034 mm a line impedance of 15.8Ω may be achieved at an operation frequency of 14.5 GHz, with an internal stripline width of 1.7676 mm. An analysis of such a structure indicates that the total loss of such a line would be 6.6 dBm$^{-1}$ (i.e. 0.066 dBcm$^{-1}$).

If the same configuration is used to achieve a line impedance of 5Ω at an operation frequency of 14.5 GHz, a stripline width of 6.1774 mm is needed, which is an increase of around 350% from the line width required to implement the 15.8Ω impedance transformer. In order for a smooth transition to take place between the impedance transformer with a line width of 1.7676 mm and the 5Ω feed line with a line width of 6.1774 mm, it is preferable to taper the 5Ω line into the 15.8Ω transformer. This may be achieved by using a 45° taper.

An analysis of the 5Ω line described above indicates that the total loss of such a line would be 6.18 dBm$^{-1}$ (0.0618 dBcm$^{-1}$). If it is assumed that the complete structure is fabricated using this particular line width, i.e. the first impedance transformer is ignored, and that the total length of the striplines between the proximal feed point and the radiating edges is 200 mm, then the total loss will be 1.236 dB. If we were to launch 47 dBm (50 W) into the structure, then we would end up with 45.764 dBm (37.705 W) total microwave power coming out of the edge of the structure. This power will be shared between the four lines disposed along the edge of the paddle, therefore each line will provide approximately 9.4 W of microwave power at 14.5 GHz. If the structure is optimised in terms of minimising impedance discontinuities and fabricated using low loss microwave substrate, this power level may be adequate to enable the desired tissue affects to be achieved.

Some of the power delivered through the spatula may be dissipated therein, which may cause the instrument to heat up undesirably. This unwanted heating may be reduced or minimised by operating the device in a pulsed mode. The pulsed mode may be a quasi-continuous mode of operation, e.g. in which the microwave source is switched off for very short periods of time during the procedure. This may reduce or minimise unwanted heating of the spatula whilst producing a consistent tissue effect at the radiating edge. In one embodiment of a quasi-continuous mode, for every 100 ms of energy delivery time the energy source may be switched off for 15 ms, and the off periods may comprise of ten periods of 1.5 ms that are evenly distributed within the 100 ms duration. Other waveforms may also be used, which are non-rectangular or regular, i.e. ramps, triangular, pseudo random sequences of pulses, etc. The waveform shape and duration (the energy delivery profile) may be based on measurements of reflected power or net power delivered into the tissue.

Figure 3:
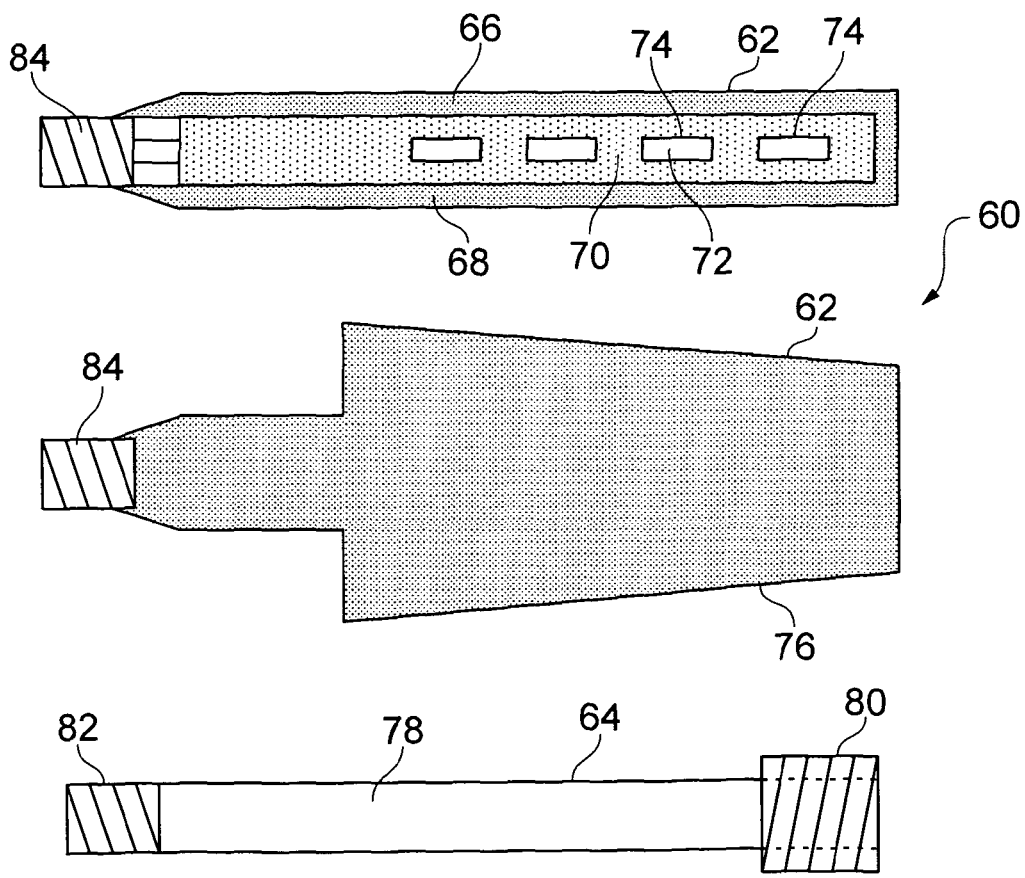
FIG. 3 shows various views of a radiating spatula that is another embodiment of the invention.

FIG. 3 shows an embodiment of a radiating spatula 60 comprising two parts 62, 64. A first part is a rigid coaxial feed line 64 that can be connected to a radiating spatula paddle 62 which uses a stripline construction as described above. The top panel in FIG. 3 shows a side view of the paddle 62, in which the metal layers 66, 68 sandwiching the dielectric material 70, that contains the microwave circuit 72 can be seen. Four radiating elements 74 are exposed at the radiating edge 76. In this embodiment, the microwave circuit 72 is arranged to match a 50Ω input with the tissue load in a similar manner to that described above.

The rigid coaxial feed line 64 comprises a cable 78, which may have a predetermined characteristic impedance e.g. of 50Ω (or 75Ω, 35Ω, 25Ω, or the like) and a SMA female connector 80 connected at the proximal end, and a SMA male connector 82 connected at the distal end. The microwave circuit 72 in the paddle 62 terminates at its distal end in an SMA launcher 84 that is received in the SMA female connector 80.

The rigid coaxial feed line 64 may have a length from 50 mm to 200 mm or more. A flexible cable assembly (not shown) may be connected to the SMA connector 82 at the proximal end of the feed line 64 to enable the microwave energy to be transported from the generator to the radiating spatula paddle 62.

The first part 64 is not limited to using a rigid coaxial feed line. It may be implemented using a second stripline structure or a microstrip structure having suitable connectors at each end, a rectangular or cylindrical waveguide structure (which may be flexible or flexibly twistable), or a flexible or semi-rigid coaxial cable assembly. For example, a 50Ω feed line may be configured with a stripline structure using the RT/duroid 5880 material mentioned above having a thickness of 0.254 mm with upper and lower metallization layers each having a thickness of 0.034 mm formed thereon. At an operation frequency of 14.5 GHz, the width of the line contained in the dielectric material can be calculated as 0.3729 mm. The total loss from such a line can be calculated as 7.93 dBm$^{-1}$ (0.0793 dBcm$^{-1}$), which implies that if the length of the first section is 100 mm, then the loss in this section is 0.793 dB, hence for 47 dBm (50 W) launch power, the power lost along this length of transmission line will be around 8 W.

In a specific embodiment, the spatula may be 10 mm wide and 1.575 mm thick with a slot open for the last 9 mm on one side-wall and a matching pin of 0.5 mm diameter on the centre-line 8 mm from the end of the spatula. The spatula board may be Rogers RT5880 ($\epsilon_r$=2.2) coated on all sides except for the slot with copper. The design assumes that the radiation is into liver with a dielectric constant of 27 and a tan δ of 0.61, and the operating frequency is 14.5 GHz To make the structure thinner, e.g. 3 mm, it would be necessary to make some significant changes, i.e. if it were made of material with a higher dielectric constant, e.g. 10, then it could be about half as wide. It could also be a bit narrower, i.e. as narrow as 4 mm.

If microstrip was used it could be thinner, but the power may not stay on the line if the liver was in contact with the top of the line. A triplate structure would be possible, as this would shield the fields from the absorber.

At 8 GHz the starting point would be about 18 mm wide, possibly getting down to 7 mm with a squeezed high dielectric version.

A further consideration in the design of the embodiments described above may be to ensure that power reflected from a radiating edge/air interface is directed into the sections of the structure that are matched with the tissue, i.e. sections of the radiating edge(s) and/or surface(s) that are in contact with the tissue. A fixed stub or filter arrangement may be implemented to ensure that the energy reflected from the mismatch is directed into the radiating sections and not back along the feed cable to the generator. This stub arrangement may also ensure that the distribution of the reflected energy is symmetrical, i.e. each radiating edge section should have the same amount of microwave power coupled into it. The length of the lines used in the design of the feed structure(s) may be arranged to direct the microwave energy to the desired locations within the microwave circuit. Balanced power splitters or couplers may be used in the design to ensure that reflected energy from sections where a mismatch occurs gets dumped or diverted efficiently.

In another embodiment, a PIN diode or a varactor switch or co-axial switch or waveguide switch may be incorporated into the structure to switch a common feed line between the two sets of radiating elements. This invention is not limited to the use of two sets of radiating elements, i.e. there may be 4 sets or 6 sets. The switching action may be performed using a switch connected to the hand-piece of the instrument, or automatically by sensing the level of reflected power and then either switch the source off or re-direct the microwave power when the level of reflected power that is above a set threshold is sensed or detected. This arrangement enables only the radiating edge that is in contact with tissue to emit microwave energy.

The radiating elements of the microwave circuit may be implemented using a leaky feeder or a travelling wave antenna arrangement where a single line with fixed characteristic impedance is used in the design of the radiating sections. For instance, a plurality of slots may be fabricated into a 50Ω transmission line, or a non-50Ω transmission line may be used with an impedance matching transformer to match the non-50Ω line to the 50Ω generator. The travelling wave structure may be implemented to allow one or both faces of the structure (top or bottom or top and bottom) to radiate uniform and focussed microwave energy into tissue. A sensing and switching arrangement using, for example, small microstrip or E-field probe couplers and power PIN switches or small co-axial switches, may be implemented within the spatula to ensure that only the face that is in contact with tissue radiates or emits microwave energy.

Figure 4:
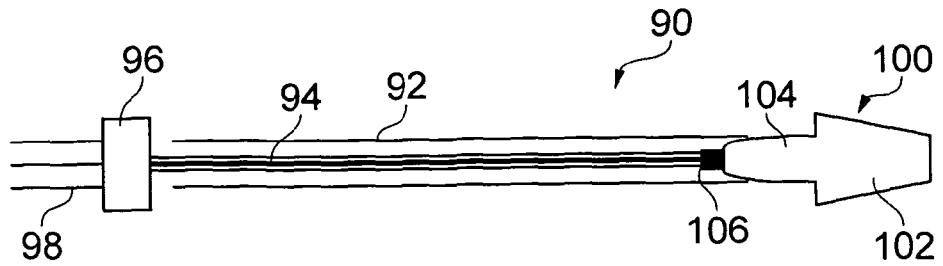
FIG. 4 is a schematic view of a surgical instrument incorporating a radiating spatula that is another embodiment of the invention.

FIG. 4 is a schematic view of another embodiment of the invention, in which the radiating spatula is used as part of a surgical instrument 90 that includes an endoscope. FIG. 4 shows the instrument channel 92 of a semi-rigid flexible controllable endoscope. The channel 92 carries a coaxial feed line 94, e.g. having a characteristic impedance of 50Ω or the like, e.g. 25Ω, 35Ω or 75Ω, that receives microwave power from a generator (not shown) via a 50Ω (or similar, i.e. 25Ω, 35Ω or 75Ω) feed line 98 and an impedance transformer 96 located outside the instrument channel 92 at the proximal end of the instrument 90. This structure is not limited to using an impedance transformer, i.e. the structure may be well matched with tissue without the transformer, e.g. the generator and delivery cable may be 35Ω and the tissue may be 35Ω. A radiating spatula 100 protrudes from the distal end of the instrument channel. The spatula has a paddle 102 with one, two or three radiating edges and/or one or two radiating faces (whose structure is as discussed above) at its distal end and a tapering plug portion 104 for fitting snugly in the instrument channel 92 to physically fix or lock the spatula in place to enable the controls at the proximal end of the endoscope to be used to manipulate or steer the paddle. A connector 106 is provided on the proximal end of the plug portion 104 to provide an interface between the microwave circuit in the spatula 100 and the coaxial feed line 94. A non-metallic adaptor (not shown), e.g. cylindrical sleeve may be attached around the interface between the coaxial feed line 94 and the plug portion 104. The adaptor provides insulation at the connection point (to prevent unwanted leakage). It may also provide a means of securing or locking or positioning the spatula 100 at the distal end of the instrument channel 92. A groove or custom locking mechanism may be provided to ensure that the radiating spatula is locked into place within the instrument channel for ease of manipulation.

Figure 5:
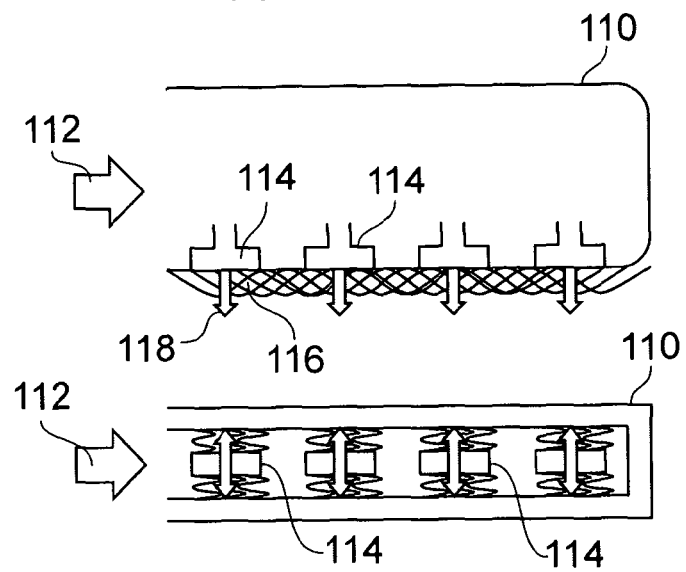
FIG. 5 shows a schematic plan and side views of the microwave radiation field emitted by a radiating spatula that is an embodiment of the invention.

FIG. 5 illustrates schematically the microwave field radiated by the spatula 110 according to the invention. As shown schematically by arrow 112, microwave energy is received into the spatula in a first direction. This energy is conveyed to the radiating elements 114 along the microwave circuit through the dielectric material. At the radiating edge, fringing fields 116 are set up which protrude from the edge in a direction 118 orthogonal to the original power feed direction (i.e. the first direction).

Figure 6:
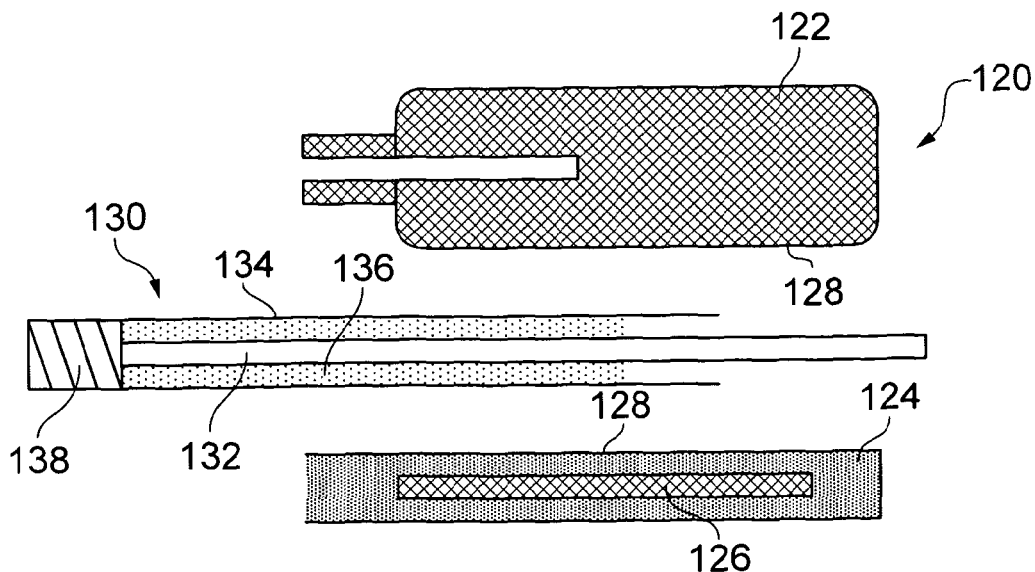
FIG. 6 shows various schematic views of a radiating spatula that is another embodiment of the invention.

FIG. 6 shows an alternative arrangement for a radiating spatula 120 according to the invention, which may be particularly well suited for use in clinical applications where small blade geometries are needed in order to allow the device to be inserted into small orifices, or where it is required to manipulate the spatula blade inside restricted regions of the human anatomy. In these particular instances, the width of the blade may be 5 mm or less and the length less than 20 mm.

In FIG. 6, the spatula 120 comprises a ceramic paddle 122 that is coated with a conductive layer 124 except at a region 126 on a side of the paddle. In this embodiment, the complete spatula may be made from hard microwave ceramic materials such as alumina or zircona covered in a metallic material in the regions where it is undesirable for the structure to radiate microwave energy. A suitable electromagnetic field simulation package, such as CST Microwave Studio or Ansoft HFSS may be used to simulate the designs and optimise the geometries, which may include integrated impedance matching transformers, i.e. quarter loaded or unloaded wavelength (or odd multiples thereof) transformers.

The top panel in FIG. 6 shows a top cross-sectional view of the ceramic paddle 122 before coating. The bottom panel is a side view after coating. In this embodiment the ceramic paddle 122 is totally covered in metallisation apart from one side edge 128. In other embodiments, the paddle may be configured to radiate along one or both side edges and/or from one or both (top and bottom) surfaces.

The ceramic material may be pure sapphire, zirconia or alumina (sapphire with glass) having a low dissipation factor (e.g. less than 0.0005) at the operation frequency and a high dielectric constant (e.g. 4 or more, i.e. 10) to enable the co-axial line with a low dielectric constant to be matched into a biological tissue with a high dielectric constant. The paddle may be coated with a biocompatible material, e.g. PTFE or Parylene C to ensure that the complete structure is biocompatible. A conformal coating of biocompatible material may be applied. The use of a biocompatible coating covering the structure (partial or complete) may allow the structure to contain one or more non-biocompatible material.

The spatula 120 further comprises a coaxial feed line 130 that has an inner conductor 132 separated from an outer conductor 134 by a dielectric material 136 (e.g. low density PTFE). A proximal end of the feed line 130 terminates with a connector 138 (e.g. SMA male connector) for connecting the spatula 120 to a generator (not shown) to receive microwave power. The ceramic paddle 122 is arranged to receive the feed line 130 at a proximal end thereof. The radiating side edge 128 extends in substantially the same direction as the feed line 130 (i.e. orthogonal to the edge of the ceramic paddle at the proximal end).

The inner and outer conductors 132, 134 extend beyond the dielectric material 136 at the distal end of the feed line. This enables part of the ceramic to be fitted inside a length of the feed line. This length may be between 5 mm and 25 mm. The section of the ceramic paddle that fits into the feed line may be ground or moulded in the shape of a cylinder with a small hole in the centre to enable the inner conductor 132 to be inserted inside. This section may perform two functions. The first function is to allow the ceramic paddle 122 to be secured to the coaxial feed cable 130, and the second function is to act as a static impedance transformer to enable the characteristic impedance of the feed cable or the generator (normally 50Ω) to be impedance matched with the impedance presented by the ceramic blade when it is in contact with the biological tissue structure that is being treated. The physical length of the cylinder may be an odd multiple of a quarter of the electrical wavelength at the frequency of operation in order to perform an impedance transformation between the 50Ω generator and the lower impedance load presented by the tissue. For example, if the inner diameter of the outer conductor used in the coaxial structure is 1.9 mm, and the outer diameter of the inner conductor is 0.51 mm, then, for a ceramic with a dielectric constant of 10, the impedance formed with the ceramic cylinder inserted into the co-axial cable is given by:

$$\frac{138}{\sqrt{10}} \log_{10}\left(\frac{1.9}{0.51}\right) = 24.93 \; \Omega.$$

If the frequency of operation is 14.5 GHz, then in order for this section to act as a transformer, the practical physical length must be either $$\frac{3 \times 10^8}{4 \times 14.5 \times 10^9 \times \sqrt{10}} = 1.64 \; mm$$

(i.e. loaded λ/4) or 4.9 mm (loaded 3λ/4). In order to ensure that the second section makes a good physical connection with the co-axial cable the 3λ/4 transformer length may be preferable.

This transformer will enable the structure to be matched into a tissue impedance of $(24.93)^2/50\Omega = 12.42\Omega$. It may be desirable to put a thread onto the ceramic cylinder and tap the inner wall of the co-axial cable to secure the radiating paddle to the co-axial structure.

The field distribution produced at the radiating edge 128 may depend on the length and configuration of the inner conductor 130 inside the ceramic paddle 122. For example, if a straight length of conductor enters the ceramic section that exists after the end of the coaxial cable then an 'E' field monopole antenna will be created. In this instance, the length of the conductor that protrudes from the end of the coaxial environment and into the ceramic should be of length that is an odd multiple of a quarter of the loaded wavelength at the frequency of interest. For example, if a ceramic is used with a dielectric constant of 10, then the length of centre conductor that should protrude from the end of the co-axial cable in order to produce an efficient monopole radiator at 14.5 GHz will be either 1.64 mm (λ/4) or 4.91 mm (3λ/4). If the centre conductor inside the ceramic section that is external to the coaxial cable is formed into a loop of wire and the length of the loop (or the circumference) is a multiple of a half the loaded wavelength at the frequency of interest (or any multiple thereof) then a 'H' field antenna will be formed inside the ceramic section.

It may also be desirable for the coaxial feed cable or line to be of non-standard characteristic impedance, i.e. not 50Ω or 75Ω, or not the same as that of the microwave generator, in order to enable the microwave energy to be transmitted more efficiently or for the physical geometry to be more preferable in terms of ease of introduction into the orifice or cannula, i.e. the characteristic impedance may be 20Ω or 120Ω. In such an arrangement, it may be desirable to include a matching transformer between the distal end of a first feed cable (between the generator and the cable introduced into the body) or the proximal end of the co-axial feed cable 130 going into the body and the microwave generator. The matching transformer may be a quarter wave (or odd multiple thereof) transformer, where the ratio of the inner diameter of the outer conductor to the outer diameter of the inner conductor and the dielectric constant of the material used to separate the two conductors determines the characteristic impedance of the transformer.

Figure 7:
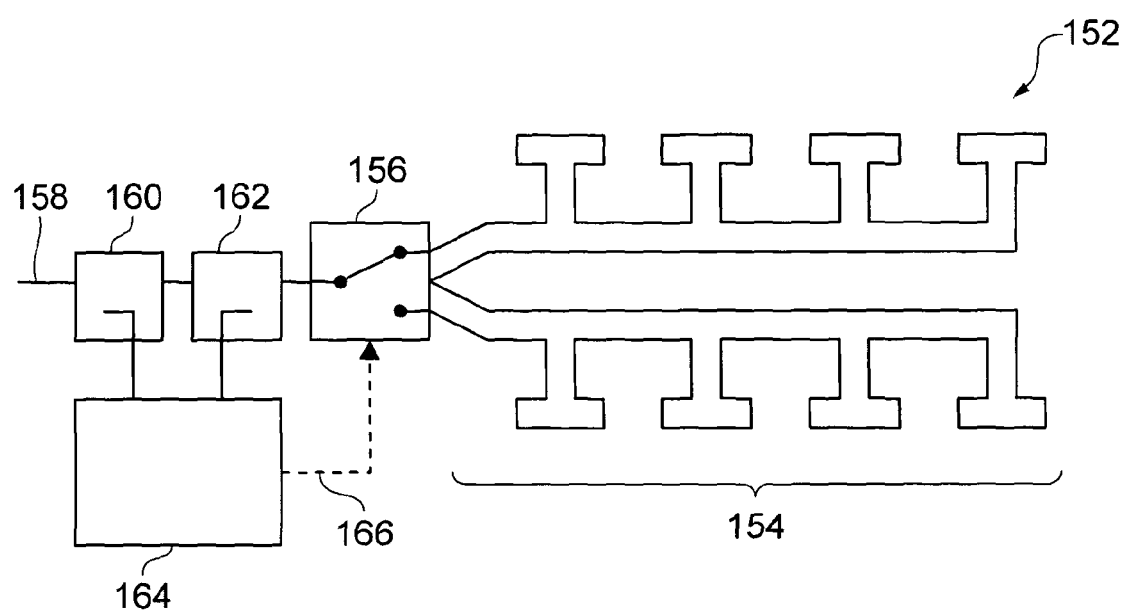
FIG. 7 shows a schematic view of a microwave circuit, switch and detector for a radiating spatula that is another embodiment of the invention.

FIG. 7 shows a schematic plan view of another microwave circuit layer 152 for a stripline structure having two selectably operable arrays 154 for opposite side edges of a spatula respectively. Each array 154 is connected to a respective output terminal of a switch 156 (e.g. a PIN diode or varactor switch). The input terminal of the switch is connected to a feed line 158 connected to receive power from the coaxial cable (not shown) connected to the handle of the spatula. Forward and reverse (reflected) power couplers 160, 162 are connected on the feed line 158 to couple part of forward and reflected signals on the feed line to a detector 164. The detector 164 may be arranged to detect magnitude and/or phase information from the forward and reflected power couplers to decide which array to feed with the microwave energy. The decision may be automatic (indicated in FIG. 7 by control signal 166) or manual, e.g. effected by a user based on display information from the detector 164 Detector 164 may take the form of a diode detector (i.e. a tunnel diode, a Schottky diode or a zero-biased Schottky diode), a homodyne detector or a heterodyne detector.

The principle clinical application of the current invention is in the treatment of polyps that exist in any part of the body. More specifically, the invention could be used to treat polyps that exist in the lining of the intestine (in particular the colon), cervix or bladder.

A polyp is an abnormal growth of tissue projecting from a mucous membrane. Polyps also occur in the nasal passages (leading to breathing difficulties) and also on the vocal cords in association with vocal nodules (giving a rasping voice). Colon polyps are a concern because they are a source of colon cancer. Conventionally, polyps are routinely removed at the time of colonoscopy either with a polypectomy snare or with biopsy forceps. The current invention enables the polyp to be removed without bleeding and the controlled microwave energy may destroy cancerous cells and prevent them from spreading. Many colorectal cancers are presently treated palliatively using much lower radio frequency energy based devices or systems that do not have the capability of reducing the tumour mass. They coagulate the raw surface of the tumour to staunch bleeding into the rectum.

Similarly, the invention may be used in the treatment of bladder cancer, e.g. to remove cells in the lining of the bladder where cancer may develop. Early stage diagnosis allows the polyp to be removed from the bladder wall—and this technology lends itself to a 'see and treat' modality in a non operating theatre environment, where the device is used in conjunction with a flexible cystoscope. Once the cancer spreads into the bladder wall, a more major operation is required.

The structures presented here may also be useful for the effective treatment of cervical cancer. In this particular instance, the radiating spatula structure may not be introduced by means of an endoscope but may be introduced directly to the inner wall of the cervix.

The invention claimed is:

1. A surgical spatula comprising a flat paddle and a handle extending away from a first end of the flat paddle, wherein:
   the handle comprises a coaxial power feed arranged to receive energy from a microwave power source, the coaxial power feed comprising an inner conductor separated from an outer conductor by a dielectric material, the inner conductor and the outer conductor extending beyond the dielectric material at a distal end of the coaxial power feed,
   the flat paddle is formed from a piece of ceramic that has an outer surface that is metal except for a non-metallised region along a side edge thereof which extends away from the first end,
   the piece of ceramic is fitted to the distal end of the coaxial power feed, whereby the metallized outer surface of the piece of ceramic is electrically connected to the outer conductor of the coaxial power feed, and the inner conductor of the coaxial power feed is received in a passageway formed in the piece of ceramic to permit a microwave radiation field to be emitted from the non-metallized region at the side edge of the flat paddle.

2. A surgical spatula according to claim 1, wherein a front end of the flat paddle opposite the first end is smooth to be unsuitable for slicing.

3. A surgical instrument comprising an endoscope and a surgical spatula according to claim 1, wherein an instrument channel of the endoscope carries a coaxial power cable, and the handle of the spatula is mountable at the distal end of the instrument channel to connect the coaxial power feed to the coaxial power cable.

4. A surgical instrument according to claim 3, wherein the width of the paddle is less than 4 mm.

5. A surgical instrument comprising:
   a surgical spatula according to claim 1; and
   endoscope; and
   wherein the microwave power source is connected to deliver microwave energy to the spatula via a microwave feed cable running through an instrument channel of the endoscope,
   wherein the handle of the surgical spatula is secured in the distal end of the instrument channel such that the paddle protrudes therefrom, and the coaxial power feed of the handle is connected to the microwave feed cable.

6. A surgical instrument according to claim 5, wherein the handle is tapered to form an interference fit with the instrument channel.

7. A surgical instrument according to claim 5, wherein the handle includes a key for locking with a corresponding keyway in the instrument channel.

8. A surgical instrument according to claim 5 including an insulating sleeve mounted to surround the interface between the microwave feed cable and the coaxial power feed on the handle.

9. A surgical instrument according claim 5 including a detector arranged to detect reflected signal information representative of an impedance match at the open side edge to control the level of power delivered to the spatula.

* * * * *